US012655759B2

(12) United States Patent
Mhanna et al.

(10) Patent No.: US 12,655,759 B2
(45) Date of Patent: Jun. 16, 2026

(54) METHOD AND SYSTEM FOR WATER CUT SENSING IN AN OIL-WATER FLOW

(71) Applicants:SAUDI ARABIAN OIL COMPANY, Dhahran (SA); King Abdullah University of Science and Technology, Thuwal-Jeddah (SA)

(72) Inventors: Mhanna Mhanna, Thuwal-Jeddah (SA); Muhammad Arsalan, Dhahran (SA); Mohamed Sy, Thuwal-Jeddah (SA); Aamir Farooq, Thuwal-Jeddah (SA)

(73) Assignees: SAUDI ARABIAN OIL COMPANY, Dhahran (SA); KING ABDULLAH UNIVERSITY OF SCIENCE AND TECHNOLOGY, Thuwal-Jeddah (SA)

( * ) Notice: Subject to any disclaimer, the term of this patent is extended or adjusted under 35 U.S.C. 154(b) by 276 days.

(21) Appl. No.: 18/535,964

(22) Filed: Dec. 11, 2023

(65) Prior Publication Data

US 2024/0200445 A1      Jun. 20, 2024

Related U.S. Application Data

(60) Provisional application No. 63/476,122, filed on Dec. 19, 2022.

(51) Int. Cl.
E21B 49/08      (2006.01)
G01F 1/74      (2006.01)
(Continued)

(52) U.S. Cl.
CPC ............ E21B 49/0875 (2020.05); G01F 1/74 (2013.01); G01N 21/359 (2013.01); G01N 33/2823 (2013.01)

(58) Field of Classification Search
CPC ..... E21B 49/0875; G01F 1/74; G01N 21/359; G01N 33/2823; G01N 33/2847
See application file for complete search history.

(56) References Cited

U.S. PATENT DOCUMENTS

| | | | |
|---|---|---|---|
| 4,891,969 A | 1/1990 | Wayland et al. | |
| 5,331,156 A | 7/1994 | Hines et al. | |
| (Continued) | | | |

FOREIGN PATENT DOCUMENTS

| | | |
|---|---|---|
| CN | 1570572 A | 1/2005 |
| CN | 206609788 U | 11/2017 |
| CN | 109187426 A | 1/2019 |

OTHER PUBLICATIONS

Mhanna, Mhanna: "CCRC Seminar—Oct. 20, 2022", Oct. 20, 2022 (Oct. 20, 2022), pp. 1-3, XP093145918, CCRC, King Abdullah University of Science and Technology (Year: 2022).*

(Continued)

*Primary Examiner* — Edwin C Gunberg
*Assistant Examiner* — Richard O Toohey
(74) *Attorney, Agent, or Firm* — Osha Bergman Watanabe & Burton LLP

(57)      ABSTRACT

A system for water cut sensing in an oil-water flow includes a laser-based spectroscopy sensor and a computer system. The laser-based spectroscopy sensor includes a first set of lasers that expose the oil-water flow to a first incident signal, a first photodetector that collects a first transmitted signal, the first transmitted signal being a component of the first incident signal transmitted through the oil-water flow, a second set of lasers that expose the oil-water flow to a second incident signal, and a second photodetector that collects a second transmitted signal, the second transmitted signal being a component of the second incident signal transmitted through the oil-water flow. The computer system (Continued)

that calculates the water cut of the oil-water flow based on the first transmitted signal and the second transmitted signal.

18 Claims, 7 Drawing Sheets

(51) Int. Cl.
  *G01N 21/359* (2014.01)
  *G01N 33/28* (2006.01)

(56) References Cited

U.S. PATENT DOCUMENTS

| | | | |
|---|---|---|---|
| 6,032,539 | A | 3/2000 | Liu et al. |
| 9,453,938 | B2 * | 9/2016 | Vijayakumar ......... G01N 21/39 |
| 9,983,126 | B2 * | 5/2018 | Kotidis .................. G01N 21/39 |
| 2012/0112072 | A1 | 5/2012 | Jones et al. |
| 2014/0020453 | A1 | 1/2014 | Estrada et al. |
| 2021/0116276 | A1 | 4/2021 | Ramakrishnan et al. |

OTHER PUBLICATIONS

G. Elseth, "An Experimental Study of Oil / Water Flow in Horizontal Pipes", Department of Technology (HiT-TF) Telemark University College Kjølnes Ring, N-3914 Porsgrunn Norway, 2021 (270 pages).

M. Qing et al., "Impedance spectroscopy dependent water content detection in dynamic oil-water emulsions", AIP Advances Mathematical Physics Collection, Oct. 5, 2018 (10 pages).

E. S. Johansen et al., "A Prototype Wet-Gas and Multiphase Flowmeter", 25th International North Sea Flow Measurement Workshop, Oct. 16-19, 2007 (16 pages).

M. A. Karimi et al., "Design and Dynamic Characterization of an Orientation Insensitive Microwave Water-Cut Sensor", IEEE Transactions On Microwave Theory and Techniques, 2017 (10 pages).

M. A. Karimi et al., "A Low Cost and Pipe Conformable Microwave-Based Water-Cut Sensor", 978-1-5090-0698-4/16/ $31.00 © 2016 IEEE (4 pages).

A. Chaudhuri et al., "An Algorithm for Determining Volume Fractions in Two-Phase Liquid Flows by Measuring Sound Speed", Journal of Fluids Engineering, Oct. 2012, vol. 134, pp. 1013001-1-101301-7 (7 pages).

C. A. Cantrell, "Technical Note: Review of methods for linear least-squares fitting of data and application to atmospheric chemistry problems", Atmospheric Chemistry and Physics, vol. 8, pp. 5477-5487, 2008 (11 pages).

D. York, "Least squares fitting of a straight line with correlated errors", Earth and Planetary Science Letters, vol. 5, (1969) pp. 320-324. North-Holland Publishing Comp., Amsterdam (5 pages).

"CCRC Seminar;" Oct. 20, 2022; pp. 1-3; XP093145918; Retrieved from the Internet: URL: https://ccrc.kaust.edu.sa/events/2022/10/20/default-calendar/CCRC-seminar-20oct-2022 (3 pages).

International Search Report and Written Opinion issued in Application No. PCT/US2023/084577, mailed on Apr. 15, 2024 (15 pages).

* cited by examiner

System for Water Cut Sensing in an Oil-Water Flow 200

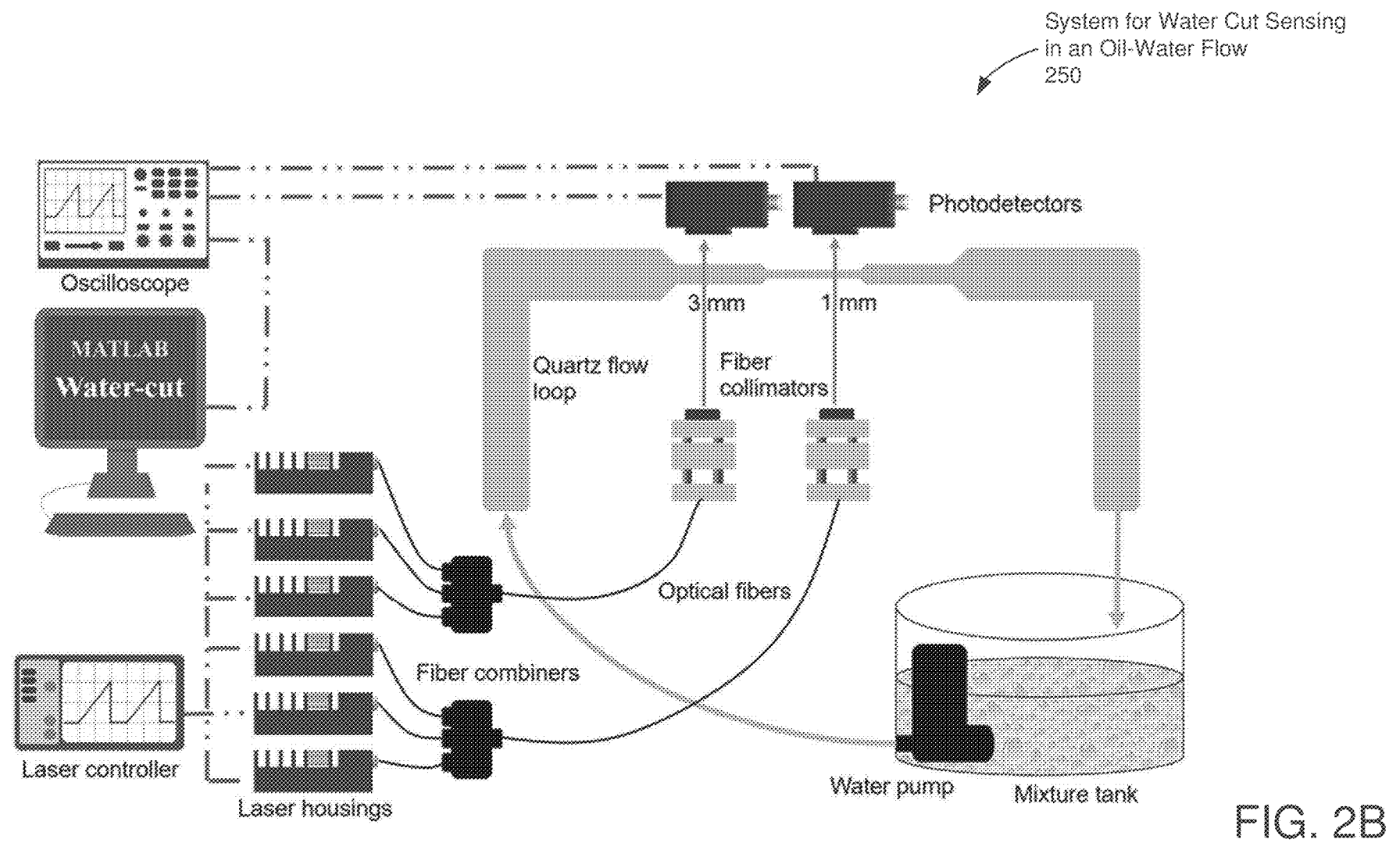

System for Water Cut Sensing
in an Oil-Water Flow
250

Photodetectors

1mm

3mm

Fiber
collimators

Optical fibers

Quartz flow
loop

Fiber combiners

Mixture tank

Water pump

Laser housings

Oscilloscope

MATLAB
Water-cut

Laser controller

FIG. 2B

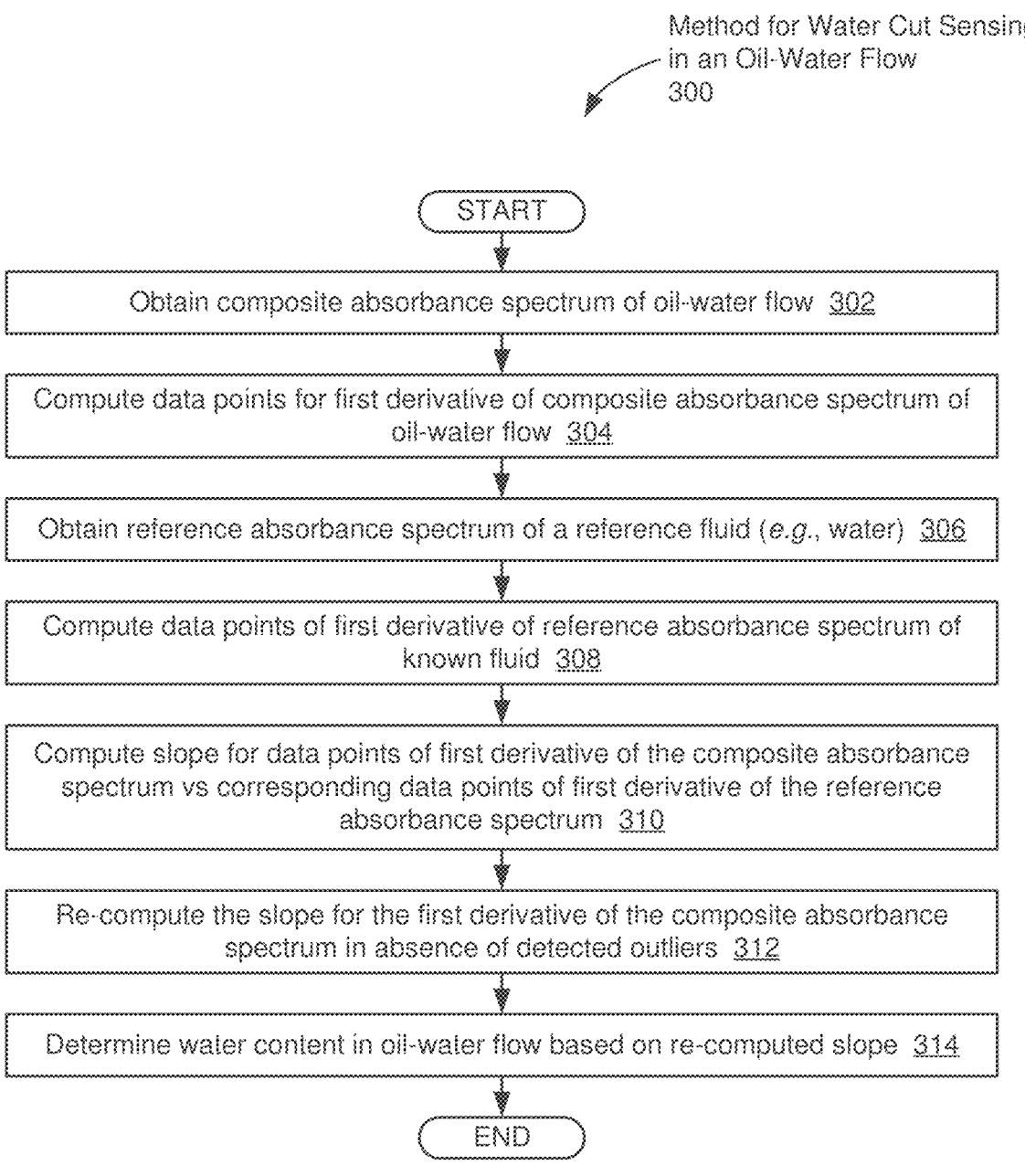

Method for Water Cut Sensing
in an Oil-Water Flow
300

START

Obtain composite absorbance spectrum of oil-water flow  302

Compute data points for first derivative of composite absorbance spectrum of oil-water flow  304

Obtain reference absorbance spectrum of a reference fluid (*e.g.*, water)  306

Compute data points of first derivative of reference absorbance spectrum of known fluid  308

Compute slope for data points of first derivative of the composite absorbance spectrum vs corresponding data points of first derivative of the reference absorbance spectrum  310

Re-compute the slope for the first derivative of the composite absorbance spectrum in absence of detected outliers  312

Determine water content in oil-water flow based on re-computed slope  314

END

FIG. 3

METHOD AND SYSTEM FOR WATER CUT SENSING IN AN OIL-WATER FLOW

BACKGROUND

Effective oil production is indispensable to fulfill the increasing energy demands of the world. Enhanced recovery methods, along with the presence of perforated rocks near the oil reservoir, can be a cause of water becoming mixed into the oil. Water cut (WC) measurement is essential in the oil industry as it is key for production allocation, reservoir management, and early water breakthrough detection. WC varies with the age and geolocation of oil wells, which requires WC sensors to span near full dynamic range (0-100%), and thus cover wide industrial applications. A myriad of WC sensors exists in literature based on various technologies. Dielectric properties of oil-water (OW) mixtures have been exploited, especially at high frequencies (MHZ), by measuring microwave resonance and transmission to detect WC. However, microwave resonance suffers poor sensitivity to WC, and microwave transmission is obfuscated in saline OW mixtures. WC can be measured intrusively by several methods, but these cannot be utilized for inline WC sensing. Multi-energy gamma rays which use radioactive sources can be used, but they are associated with handling and disposal safety concerns. Planar microwave resonance has been implemented on a pipeline surface to provide in situ, non-intrusive WC sensing. However, calibration was needed to know what oils were present in the OW flow. Near-infrared (NIR) spectroscopy has been employed based on adapting Beer-Lambert law for non-homogeneous immiscible mixtures, and although the resulting WC sensor was proven to be more accurate than other sensors, it needs frequent well-specific calibration which gets tedious with well-aging and changing geolocation. Accordingly, alternative WC sensors that operate in the full dynamic range (0-100%), and that do not require any calibration would be highly desirable and beneficial.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a system for water cut sensing in an oil-water flow, the system comprising: a laser-based spectroscopy sensor comprising: a first plurality of lasers that expose the oil-water flow to a first incident signal; a first photodetector that collects a first transmitted signal, the first transmitted signal being a component of the first incident signal transmitted through the oil-water flow; a second plurality of lasers that expose the oil-water flow to a second incident signal; and a second photodetector that collects a second transmitted signal, the second transmitted signal being a component of the second incident signal transmitted through the oil-water flow; and a computer system that calculates the water cut of the oil-water flow based on the first transmitted signal and the second transmitted signal.

In general, in one aspect, embodiments relate to a method for water cut sensing in an oil-water flow, the method comprising: exposing the oil-water flow to a first incident signal emitted by a first plurality of lasers; collecting, by a first photodetector, a first transmitted signal, the first transmitted signal being a component of the first incident signal transmitted through the oil-water flow; exposing the oil-water flow to a second incident signal emitted by a second plurality of lasers; and collecting, by a second photodetector, a second transmitted signal, the second transmitted signal being a component of the second incident signal transmitted through the oil-water flow; and calculating the water cut of the oil-water flow based on the first transmitted signal and the second transmitted signal.

In light of the structure and functions described above, embodiments of the disclosure may include respective means adapted to carry out various steps and functions defined above in accordance with one or more aspects and any one of the embodiments of one or more aspect described herein.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

FIGS. 2A and 2B show systems for water cut sensing in an oil-water flow in accordance with one or more embodiments.

FIG. 3 shows a flowchart for a method in accordance with one or more embodiments.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Water cut (WC) measurement is essential in the oil industry as it is key for production allocation, reservoir management, and early water breakthrough detection. WC varies with the age and geolocation of oil wells, which requires WC sensors to span near full dynamic range (0-100%), and thus cover wide industrial applications.

In general, embodiments of the disclosure include systems and methods for WC sensing in an oil-water flow. The following discussion provides a description of scenarios that require or benefit from the availability of accurate WC measurements, followed by a description of the components of systems for WC sensing and operations performed by these systems.

Figure 1:
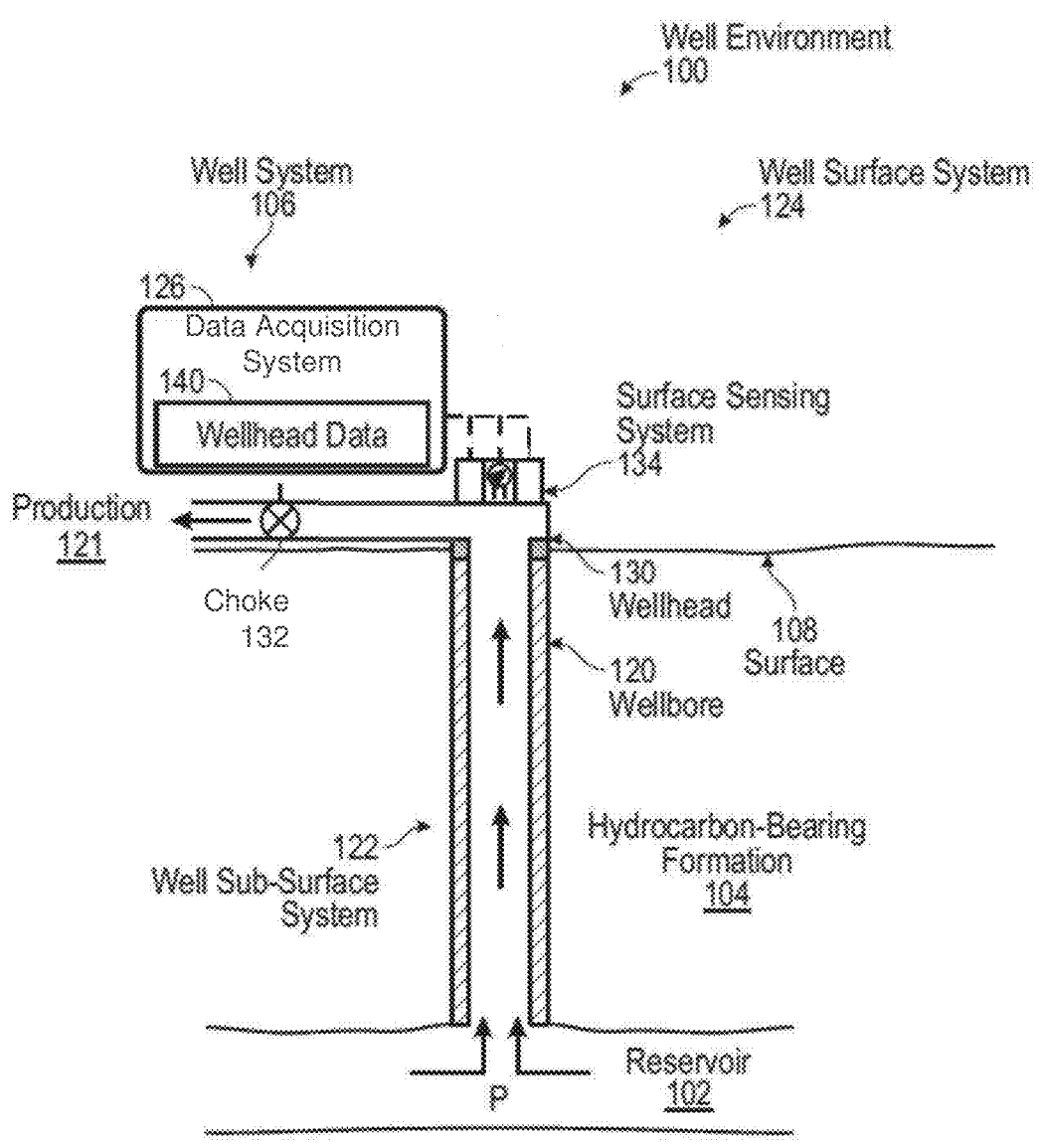
FIG. 1 shows a well environment in accordance with one or more embodiments.

FIG. 1 shows a schematic diagram in accordance with one or more embodiments. FIG. 1 illustrates a well environment (100) that includes a hydrocarbon reservoir ("reservoir") (102) located in a subsurface hydrocarbon-bearing formation (104) and a well system (106). The hydrocarbon-bearing formation (104) may include a porous or fractured rock formation that resides underground, beneath the earth's surface ("surface") (108). In the case of the well system (106) being a hydrocarbon well, the reservoir (102) may include a portion of the hydrocarbon-bearing formation (104). The hydrocarbon-bearing formation (104) and the reservoir (102) may include different layers of rock having varying characteristics, such as varying degrees of permeability, porosity, and resistivity. In the case of the well system (106) being operated as a production well, the well system (106) may facilitate the extraction of hydrocarbons (or "production") from the reservoir (102). In the case of the well system (106) being operated as an injection well, the well system (106) may be used in a tertiary recovery method to displace the produced hydrocarbons and/or to maintain the pressure profile of the reservoir (102).

In some embodiments, the well system (106) includes a wellbore (120), a well sub-surface system (122), a well surface system (124), and a data acquisition system (126). The data acquisition system (126) may monitor and/or control various operations of the well system (106), such as well production operations, well completion operations, well maintenance operations, and reservoir monitoring, assessment and development operations. In some embodiments, the data acquisition system (126) includes a computer system that is the same as or similar to that of computer system (502) described below in FIG. 6 and the accompanying description.

The wellbore (120) may include a bored hole that extends from the surface (108) into a target zone of the hydrocarbon-bearing formation (104), such as the reservoir (102). An upper end of the wellbore (120), terminating at or near the surface (108), may be referred to as the "up-hole" end of the wellbore (120), and a lower end of the wellbore, terminating in the hydrocarbon-bearing formation (104), may be referred to as the "downhole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the hydrocarbon-bearing formation (104) or the reservoir (102) during injection operations, or the communication of monitoring devices (e.g., logging tools) into the hydrocarbon-bearing formation (104) or the reservoir (102) during monitoring operations (e.g., during in situ logging operations).

In some embodiments, during operation of the well system (106), the data acquisition system (126) collects and records wellhead data (140) for the well system (106) and other data regarding downhole equipment and downhole sensors. The wellhead data (140) may include, for example, a record of measurements of wellhead pressure (P) (e.g., including flowing wellhead pressure (FWHP)), wellhead temperature (T) (e.g., including flowing wellhead temperature), wellhead production rate (R) over some or all of the life of the well (106), and/or water cut (WC) data. In some embodiments, the measurements are recorded in real-time, and are available for review or use within seconds, minutes or hours of the condition being sensed (e.g., the measurements are available within 1 hour of the condition being sensed). In such an embodiment, the wellhead data (140) may be referred to as "real-time" wellhead data (140). Real-time wellhead data (140) may enable an operator of the well to assess a relatively current state of the well system (106), and make real-time decisions regarding development of the well system (106) and the reservoir (102), such as on-demand adjustments in regulation of production flow from the well or injection flow to the well.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more chokes (132) that are operable to control the flow of production (121).

Keeping with FIG. 1, in some embodiments, the well surface system (124) includes a surface sensing system (134). The surface sensing system (134) may include sensor devices for sensing characteristics of substances, including production (121), passing through or otherwise located in the well surface system (124). The characteristics may include, for example, pressure, temperature and flow rate of production (121) flowing through the wellhead (130), or other conduits of the well surface system (124), after exiting the wellbore (120).

In some embodiments, well intervention operations may also be performed at a well site. For example, well intervention operations may include various operations carried out by one or more service entities for an oil or gas well during its productive life (e.g., fracking operations, CT, flow back, separator, pumping, wellhead and production tree maintenance, slickline, braded line, coiled tubing, snubbing, workover, subsea well intervention, etc.). For example, well intervention activities may be similar to well completion operations, well delivery operations, and/or drilling operations in order to modify the state of a well or well geometry. In some embodiments, well intervention operations are used to provide well diagnostics, and/or manage the production of the well.

In one or more embodiments, the well system (106) further includes a system for WC sensing (not shown). As previously noted, WC measurements may be used for the purposes of production allocation, reservoir management, early water breakthrough detection, etc. A system for WC sensing is subsequently discussed in reference to the remaining figures.

While FIG. 1 shows various configurations of hardware components and/or software components, other configurations may be used without departing from the scope of the disclosure. For example, various components in FIG. 1 may be combined to create a single component. As another example, the functionality performed by a single component may be performed by two or more components.

Figure 2A:
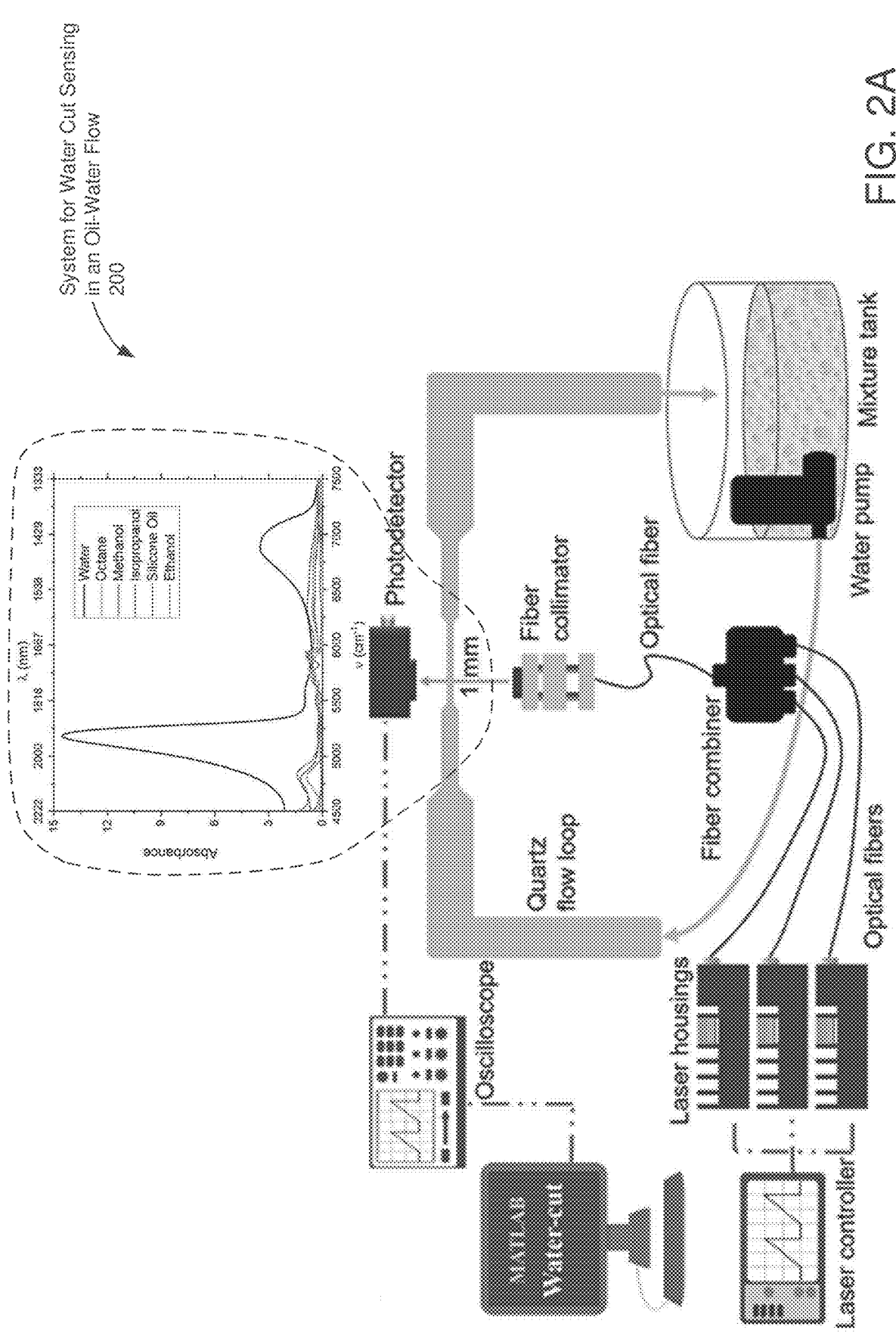

FIGS. 2A and 2B show systems (200, 250) for water cut sensing in an oil-water flow in accordance with one or more embodiments. The systems (200, 250) implement laser-based absorption spectroscopy, operating in the near-infrared (NIR) range for accurate water detection in the full dynamic rage (0-100% oil vs water) that may be used without requiring calibration.

The systems (200, 250) in accordance with embodiments of the disclosure uses NIR spectroscopy to measure the WC and rely on water having strong absorption lines in the infrared (IR) wavelength region. Example recordings of absorbance are shown for the NIR spectroscopy performed for water, but also for octane, methanol, isopropanol, silicone oil and ethanol which may be considered oil representative species. In one or more embodiments, the range of 4500-7500 cm$^{-1}$ (~1300-2200 nm) is used for measuring the full range of water concentration (0-100%) with a minimum interference from oil. For example, the high peak near 1900 nm (5210-5270 cm$^{-1}$) may be analyzed for water concentrations below 10%, while the lower peak near 1400 nm (7140-7200 cm$^{-1}$) may be used to measure higher concentrations.

As illustrated in FIGS. 2A and 2B, a quartz flow loop may be used to circulate an oil-water mixture. The NIR spectroscopy is performed through the quartz flow loop. The oil-water mixture may be obtained from a well environment as previously described.

The system (200) includes three lasers, whereas the system (250) includes six lasers. Each of the lasers may be able to scan a spectral range of 20 cm$^{-1}$.

More specifically, in the system (200), three fiber-coupled quantum cascade lasers (QCLs) (e.g., Nanoplus QCLs) emitting near 1.4 μm with an output power of, for example, ~10 mW are combined using a fiber combiner and collimated towards the target OW mixture to expose the OW mixture to an incident signal. Optical fibers may be utilized to carry the incident signal from the lasers to the water-coil flow in the pipe of the quartz flow loop and from the pipe to photodetectors. Driven by a laser controller, the lasers may be scanned at a frequency of 50 Hz to scan a tuning range of 7140-7200 cm$^{-1}$. A pump (e.g., a 20 W DC-powered pump) may be used to circulate the OW mixture through the quartz flow loop with a 1 mm sampling length. The transmitted signal may be collected by a photodetector (e.g., a DC-coupled, TE-cooled photodetector with a bandwidth of 25 MHz, Thorlabs). In one embodiment, an 83 mm silica etalon is utilized to convert the scan time to wavenumbers. The NIR spectroscopy data obtained from the detectors may be processed by a computer system as further discussed below. Further, the NIR spectroscopy data may be visualized, e.g., using an oscilloscope.

In the system (250), while generally similar to the system (200), three distributed feedback (DFB) lasers (e.g., Nanoplus DFB lasers) are used to scan the spectral range of 7140-7200 cm$^{-1}$, and three additional lasers are used to scan the range of 5210-5270 cm$^{-1}$. In one embodiment, the sampling length is 1 mm. Other sampling lengths may be used. For example, in order to detect low concentration measurements, the laser may be propagated through a 3-mm section to increase water absorbance, thereby reducing errors.

While FIGS. 2A and 2B show particular configurations of systems, variations of these systems may be used, without departing from the disclosure. For example, various optical elements may be arranged differently, and different and/or additional optical elements may be used, without departing from the disclosure. For example, any number and any types of lasers may be used, the sampling length may be varied, etc.

FIG. 3 shows a method for water cut sensing in an oil-water flow, in accordance with one or more embodiments. The method enables a determination of the water cut in an oil-water flow without the need for calibration or knowing the types of oils in the flow. Briefly summarized, the algorithm reduces or minimizes the effect of interfering absorbance to isolate the absorbance of water, thereby enabling an accurate prediction of the water cut without prior calibration. The calibration-free WC sensing is enabled by identifying and eliminating interference from non-water (e.g., oil) species in the oil-water flow as subsequently discussed. More specifically, a slope in data points obtained for absorbance is calculated for the composite absorbance spectrum of the oil-water flow vs. the corresponding data points obtained for an absorbance spectrum of a reference fluid (e.g., water), and a fitting algorithm is applied to eliminate the effect of non-water (e.g., oil) species on the slope. The slope itself may be indicative of water concentration.

Figure 6:
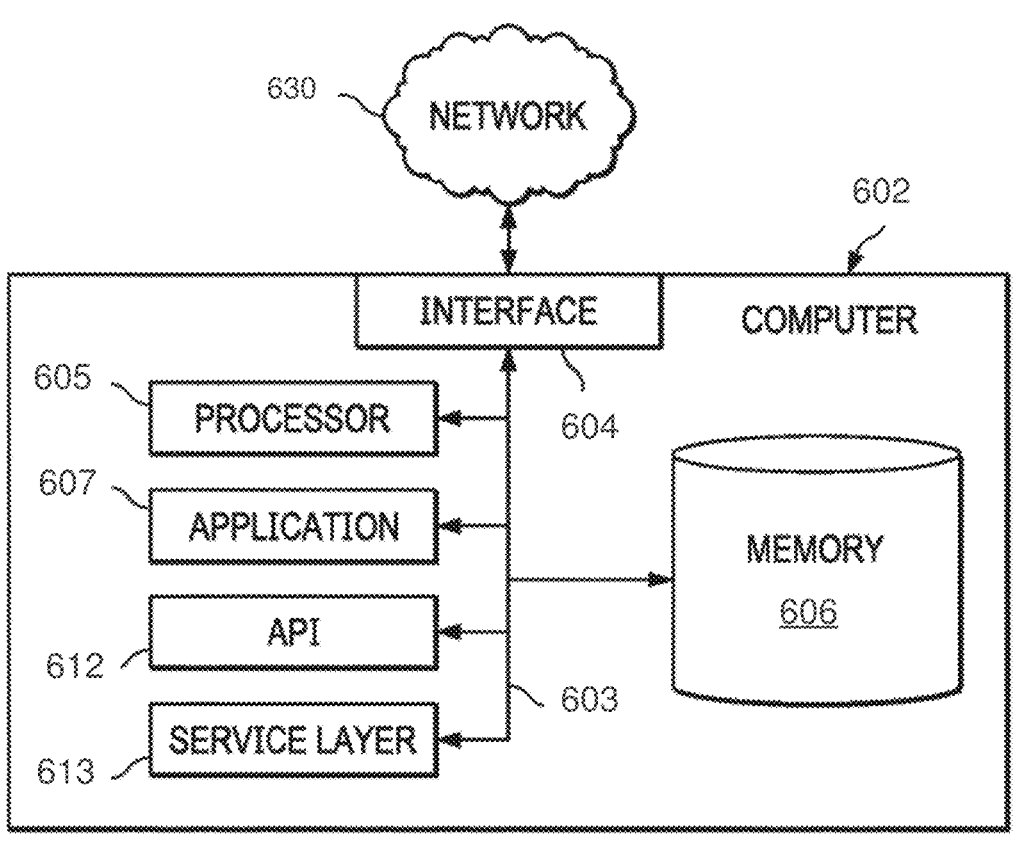
FIG. 6 shows a computer system in accordance with one or more embodiments.

The method may be implemented using instructions stored on a non-transitory medium that may be executed by a computer system as shown in FIG. 6.

While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Step 302, a composite absorbance spectrum of an oil-water flow is obtained. The composite absorbance spectrum may be obtained using systems as shown in FIGS. 2A and 2B. Briefly summarized, a laser signal is propagated through the oil-water flow and collected via a photodetector. The Beer-Lambert law is used to quantify the composite absorbance (across the spectrum) from the laser intensity attenuation. The composite absorbance is a result of the absorbance of water and/or oil in the flow.

In Step 304, data points are obtained for the first derivative of the composite absorbance spectrum of the oil-water flow. The first derivative may be computed between consecutive wavelength intervals. Any method for computing a derivative may be used.

In Step 306, a reference absorbance spectrum of a reference fluid is obtained. The reference fluid may be water, and the reference absorbance spectrum may be obtained from a database.

In Step 308, data points are obtained for the first derivative of the absorbance spectrum of water. The first derivative may be computed between consecutive wavelength intervals. Any method for computing a derivative may be used.

In Step 310, a slope is computed for the data points of the first derivative of the composite absorbance spectrum vs the corresponding data points of the first derivative of the reference absorbance spectrum. The slope may be computed by performing a linear fit. An example for the execution of Step 310 is provided in FIG. 4, left panel, showing the data points plotted in 2D space, and a linear fit line.

Figure 4:
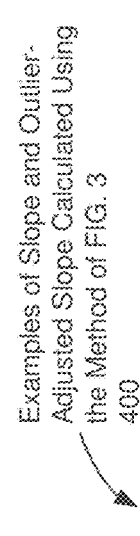
FIG. 4 shows examples of slopes before and after outlier removal in accordance with one or more embodiments.

In Step 312, the slope is re-computed. First, a threshold distance may be defined to eliminate outliers in the data points of the first derivative of the composite absorbance spectrum. The distance may be any distance (e.g., an Euclidean distance) from the linear fit line. The threshold distance may be determined by experimentation or simulation. Specifically, different threshold distances may be used for the execution of the method of FIG. 3, and the threshold distance providing the best (most accurate water cut prediction) results may be selected for use. Next, outliers in the 2D space are determined using the threshold distance. Data points that are beyond the threshold distance are eliminated from further fits or calculations. After the removal of the outliers, the slope is re-calculated. An example of calculating the slope before and after outlier removal is discussed below in reference to FIG. 4. The left panel of FIG. 4 illustrates the calculation of the slope prior to outlier removal, and the right panel of FIG. 4 illustrates the calculation of the slope after outlier removal.

In Step 314, the water content in the oil-water content is determined based on the re-computed slope. For a reference absorbance spectrum that is based on 100% water, the water content (in %) is directly represented by the slope itself. For a reference absorbance spectrum that is based on a reference fluid that is an oil-water mix, the slope may be multiplied with the percentage of water in the oil-water mix of the reference fluid. For example, for a reference fluid that contains 90% water, the outlier-adjusted slope may be multiplied by 0.9.

The described steps may be performed for different wavelengths/wavenumbers. As shown in the spectrum included in FIG. 2A, the absorbance of water includes a weaker peak near 7150 $cm^{-1}$ and a stronger peak near 5250 $cm^{-1}$. The former may be used to measure high water cuts, and the latter may be used to measure low water cuts. An advantage of using different peaks for different water cuts is that it allows the absorbance to be kept within a certain range (e.g., 0.01-3.5) to achieve a better signal-to-noise ratio. Accordingly, the calculations that result in the slope and the outlier-adjusted slope may be based on different regions of the absorbance spectra, depending on the prevalent water cut. Proper wavenumber intervals may, thus, be selected from the full absorbance spectra, based on this consideration. In an implementation of the method, an "if" statement may be used to automate the above selection. First, the region at the stronger peak may be used to calculate the water cut. If the obtained reading is below 10%, the reading is assumed to be accurate. However, if the reading is above 10%, the execution of the method may be repeated for the region at the weaker peak.

The steps of the described method may be repeatedly performed over time, e.g., in a loop. Accordingly, the system and method as described may continuously provide updated readings on the water cut in the oil-water flow.

FIG. 4 shows examples (400) of slopes before and after outlier removal, calculated using the method of FIG. 3. The plot in the left panel of FIG. 4 shows a slope generated in presence of outliers. The slope may have been obtained by execution of Step 310 of the method described in FIG. 3. The plot in the right panel of FIG. 4 shows an outlier-adjusted slope after removal of the outlier. The outlier-adjusted slope may have been obtained by execution of Step 312 of the method described in FIG. 3.

Figure 5:
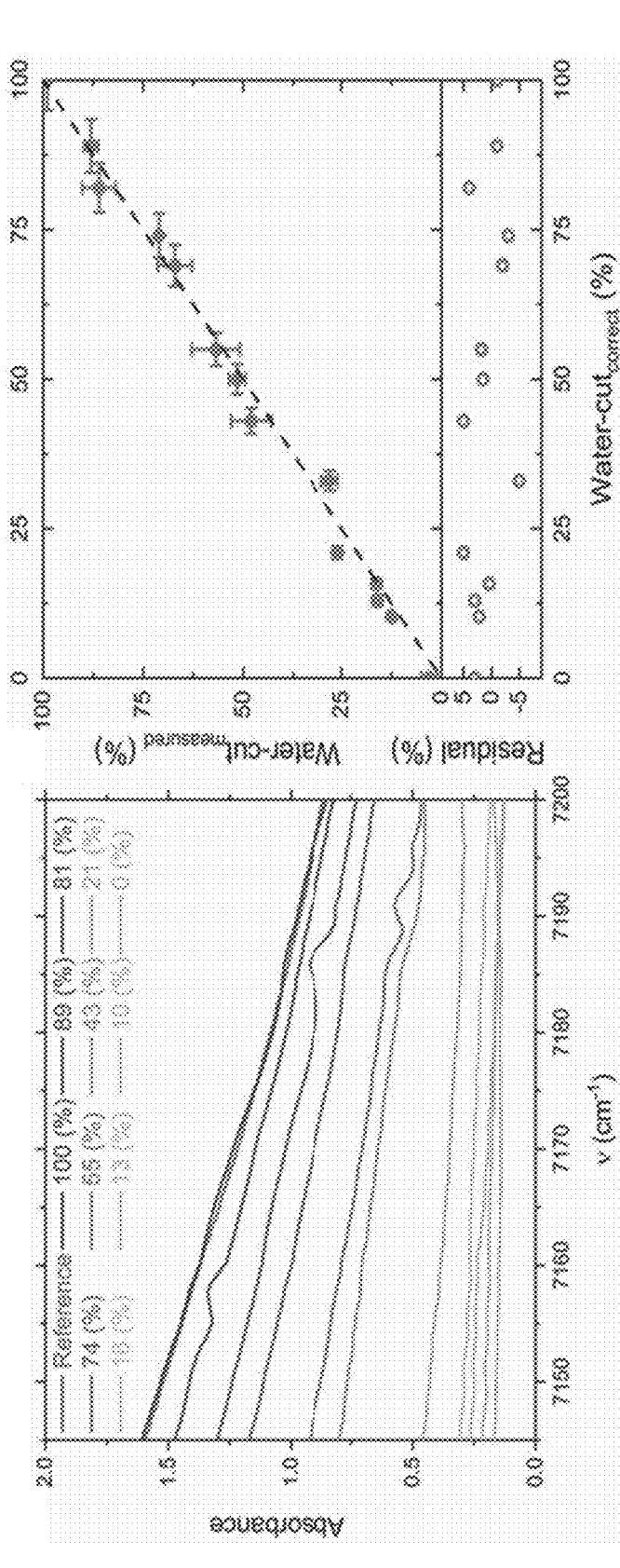
FIG. 5 shows performance examples in accordance with one or more embodiments.

FIG. 5 shows performance examples (500). The plot in the left panel of FIG. 5 illustrates measured absorbance spectra obtained for oil-water mixtures with a water cut ranging from 0% to 100% and a comparison to a simulated pure water spectrum. The plot in the right panel of FIG. 5 visualizes the residual error in a comparison of measured water cut and actual water cut. As the plot shows, residuals remained in a range of +/−5%.

Embodiments of the disclosure have various beneficial characteristics. For example, embodiments of the disclosure provide an accurate sensing of the water cut in an oil-water flow, without requiring a calibration and without knowing the species present in the oil-water flow. Embodiments of the disclosure are robust against signal attenuation by laser scatting due to particles, salinity effects, and high temperature effects.

Embodiments may be implemented on a computer system. FIG. 6 is a block diagram of a computer system (602) used to provide computational functionalities associated with described algorithms, methods, functions, processes, flows, and procedures as described in the instant disclosure, according to an implementation. The illustrated computer (602) is intended to encompass any computing device such as a high-performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (602) may include a computer that includes an input device, such as a keypad, keyboard, touch screen, or other device that can accept user information, and an output device that conveys information associated with the operation of the computer (602), including digital data, visual, or audio information (or a combination of information), or a GUI.

The computer (602) can serve in a role as a client, network component, a server, a database or other persistency, or any other component (or a combination of roles) of a computer system for performing the subject matter described in the instant disclosure. The illustrated computer (602) is communicably coupled with a network (630). In some implementations, one or more components of the computer (602) may be configured to operate within environments, including cloud-computing-based, local, global, or other environment (or a combination of environments).

At a high level, the computer (602) is an electronic computing device operable to receive, transmit, process, store, or manage data and information associated with the described subject matter. According to some implementations, the computer (602) may also include or be communicably coupled with an application server, e-mail server, web server, caching server, streaming data server, business intelligence (BI) server, or other server (or a combination of servers).

The computer (602) can receive requests over network (630) from a client application (for example, executing on another computer (602)) and responding to the received requests by processing the said requests in an appropriate software application. In addition, requests may also be sent to the computer (602) from internal users (for example, from a command console or by other appropriate access method), external or third-parties, other automated applications, as well as any other appropriate entities, individuals, systems, or computers.

Each of the components of the computer (602) can communicate using a system bus (603). In some implementations, any or all of the components of the computer (602), both hardware or software (or a combination of hardware and software), may interface with each other or the interface (604) (or a combination of both) over the system bus (603) using an application programming interface (API) (612) or a service layer (613) (or a combination of the API (612) and service layer (613). The API (612) may include specifications for routines, data structures, and object classes. The API (612) may be either computer-language independent or dependent and refer to a complete interface, a single function, or even a set of APIs. The service layer (613) provides software services to the computer (602) or other components (whether or not illustrated) that are communicably coupled to the computer (602). The functionality of the computer (602) may be accessible for all service consumers using this service layer. Software services, such as those provided by the service layer (613), provide reusable, defined business functionalities through a defined interface. For example, the interface may be software written in JAVA, C++, or other suitable language providing data in extensible markup language (XML) format or other suitable format. While illustrated as an integrated component of the computer (602), alternative implementations may illustrate the API (612) or the service layer (613) as stand-alone components in relation to other components of the computer (602) or other components (whether or not illustrated) that are communicably coupled to the computer (602). Moreover, any or all parts of the API (612) or the service layer (613) may be implemented as child or sub-modules of another software module, enterprise application, or hardware module without departing from the scope of this disclosure.

The computer (602) includes an interface (604). Although illustrated as a single interface (604) in FIG. 6, two or more interfaces (604) may be used according to particular needs, desires, or particular implementations of the computer (602). The interface (604) is used by the computer (602) for communicating with other systems in a distributed environment that are connected to the network (630). Generally, the interface (604 includes logic encoded in software or hardware (or a combination of software and hardware) and operable to communicate with the network (630). More specifically, the interface (604) may include software supporting one or more communication protocols associated with communications such that the network (630) or interface's hardware is operable to communicate physical signals within and outside of the illustrated computer (602).

The computer (602) includes at least one computer processor (605). Although illustrated as a single computer processor (605) in FIG. 6, two or more processors may be used according to particular needs, desires, or particular implementations of the computer (602). Generally, the computer processor (605) executes instructions and manipulates data to perform the operations of the computer (602) and any algorithms, methods, functions, processes, flows, and procedures as described in the instant disclosure.

The computer (602) also includes a memory (606) that holds data for the computer (602) or other components (or a combination of both) that can be connected to the network (630). For example, memory (606) can be a database storing data consistent with this disclosure. Although illustrated as a single memory (606) in FIG. 6, two or more memories may be used according to particular needs, desires, or particular implementations of the computer (602) and the described functionality. While memory (606) is illustrated as an integral component of the computer (602), in alternative implementations, memory (606) can be external to the computer (602).

The application (607) is an algorithmic software engine providing functionality according to particular needs, desires, or particular implementations of the computer (602), particularly with respect to functionality described in this disclosure. For example, application (607) can serve as one or more components, modules, applications, etc. Further, although illustrated as a single application (607), the application (607) may be implemented as multiple applications (607) on the computer (602). In addition, although illustrated as integral to the computer (602), in alternative implementations, the application (607) can be external to the computer (602).

There may be any number of computers (602) associated with, or external to, a computer system containing computer (602), each computer (602) communicating over network (630). Further, the term "client," "user," and other appropriate terminology may be used interchangeably as appropriate without departing from the scope of this disclosure. Moreover, this disclosure contemplates that many users may use one computer (602), or that one user may use multiple computers (602).

In some embodiments, the computer (602) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, a cloud computing system may operate according to one or more service models, such as infrastructure as a service (IaaS), platform as a service (PaaS), software as a service (Saas), mobile "backend" as a service (MBaaS), serverless computing, artificial intelligence (AI) as a service (AIaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A system for water cut sensing in an oil-water flow, the system comprising:
    a laser-based spectroscopy sensor comprising:
        a quartz flow loop accommodating the oil-water flow;
        a first plurality of lasers that expose the oil-water flow to a first incident signal;
        a first photodetector that collects a first transmitted signal, the first transmitted signal being a component of the first incident signal transmitted through the oil-water flow;
        a second plurality of lasers that expose the oil-water flow to a second incident signal;
        and a second photodetector that collects a second transmitted signal, the second transmitted signal being a component of the second incident signal transmitted through the oil-water flow; and
    a computer system that calculates the water cut of the oil-water flow based on the first transmitted signal and the second transmitted signal.

2. The system of claim 1, wherein the first plurality of lasers comprises three distributed feedback lasers.

3. The system of claim 1, wherein each laser of the first plurality of lasers and each laser of the second plurality of lasers is configured to scan a spectral range of 20 cm$^{-1}$.

4. The system of claim 1, wherein the first plurality of lasers is configured to scan a spectral range of 7140-7200 cm$^{-1}$.

5. The system of claim 1, wherein the second plurality of lasers is configured to scan a spectral range of 5210-5270 cm$^{-1}$.

6. The system of claim 1, wherein the quartz flow loop comprises a section providing a 1 mm sampling length for the laser-based spectroscopy sensor.

7. The system of claim 1, wherein the quartz flow loop comprises a section providing a 3 mm sampling length for the laser-based spectroscopy sensor.

8. The system of claim 1, further comprising:

a pump that establishes the oil-water flow in the quartz flow loop.

9. The system of claim 1, further comprising:

a first fiber combiner that combines outputs of the first plurality of lasers to form the first incident signal; and a second fiber combiner that combines outputs of the second plurality of lasers to form the second incident signal.

10. A method for water cut sensing in an oil-water flow, the method comprising:

exposing the oil-water flow circulating in a quartz flow loop to a first incident signal emitted by a first plurality of lasers;

collecting, by a first photodetector, a first transmitted signal, the first transmitted signal being a component of the first incident signal transmitted through the oil-water flow;

exposing the oil-water flow to a second incident signal emitted by a second plurality of lasers; and collecting, by a second photodetector, a second transmitted signal, the second transmitted signal being a component of the second incident signal transmitted through the oil-water flow; and calculating the water cut of the oil-water flow based on the first transmitted signal and the second transmitted signal.

11. The method of claim 10, wherein the first plurality of lasers comprises three distributed feedback lasers.

12. The method of claim 10, wherein each laser of the first plurality of lasers and each laser of the second plurality of lasers is configured to scan a spectral range of 20 $\text{cm}^{-1}$.

13. The method of claim 10, wherein the first plurality of lasers is configured to scan a spectral range of 7140-7200 $\text{cm}^{-1}$.

14. The method of claim 10, wherein the second plurality of lasers is configured to scan a spectral range of 5210-5270 $\text{cm}^{-1}$.

15. The method of claim 10, wherein the quartz flow loop comprises a section providing a 1 mm sampling length for the laser-based spectroscopy sensor.

16. The method of claim 10, wherein the quartz flow loop comprises a section providing a 3 mm sampling length for the laser-based spectroscopy sensor.

17. The method of claim 10, further comprising establishing the oil-water flow in the quartz flow loop by a pump.

18. The method of claim 10, further comprising:

combining, using a first fiber combiner, outputs of the first plurality of lasers to form the first incident signal; and combining, using a second fiber combiner, outputs of the second plurality of lasers to form the second incident signal.

\* \* \* \* \*